US011622720B2

United States Patent
Prot et al.

(10) Patent No.: US 11,622,720 B2
(45) Date of Patent: Apr. 11, 2023

(54) DISTURBANCES INDICATOR FOR A WEARABLE DEVICE

(71) Applicant: BIOSERENITY, Paris (FR)

(72) Inventors: Pierre Prot, Paris (FR); Pierre-Yves Frouin, Paris (FR)

(73) Assignee: BioSerenity, Paris (FR)

( * ) Notice: Subject to any disclaimer, the term of this patent is extended or adjusted under 35 U.S.C. 154(b) by 912 days.

(21) Appl. No.: 16/472,432

(22) PCT Filed: Dec. 22, 2017

(86) PCT No.: PCT/FR2017/053832
§ 371 (c)(1),
(2) Date: Jun. 21, 2019

(87) PCT Pub. No.: WO2018/122522
PCT Pub. Date: Jul. 5, 2018

(65) Prior Publication Data
US 2019/0357846 A1  Nov. 28, 2019

(30) Foreign Application Priority Data
Dec. 26, 2016 (FR) ........................... 1663387

(51) Int. Cl.
*A61B 5/05* (2021.01)
*A61B 5/00* (2006.01)
(Continued)

(52) U.S. Cl.
CPC ............ *A61B 5/6804* (2013.01); *A61B 5/053* (2013.01); *A61B 5/25* (2021.01); *A61B 5/7217* (2013.01);
(Continued)

(58) Field of Classification Search
CPC ......... A61B 5/6804; A61B 5/053; A61B 5/25; A61B 5/7217; A61B 2560/0209;
(Continued)

(56) References Cited

U.S. PATENT DOCUMENTS

| 2009/0318827 | A1 | 12/2009 | Freer |
| 2015/0015452 | A1 | 1/2015 | Chang et al. |
| 2016/0022216 | A1* | 1/2016 | Goldshtein ............... H02J 7/06 600/486 |

FOREIGN PATENT DOCUMENTS

| EP | 2 407 096 A1 | 1/2012 |
| WO | WO2005/048824 A2 | 6/2005 |

OTHER PUBLICATIONS

International Search Report dated Apr. 20, 2018 in corresponding International Application No. PCT/FR2017/053832; 6 pages.
(Continued)

*Primary Examiner* — Rex R Holmes
(74) *Attorney, Agent, or Firm* — Lee & Hayes, P.C.

(57) ABSTRACT

A system for measuring disturbances, which is intended to be worn by a user, the system including at least one bioelectric measurement element; an analogue-to-digital conversion device electrically connected to the at least one bioelectric measurement element; and at least one conductive track electrically connected to a ground of the system by use of a resistor and an input of the analogue-to-digital conversion device. Also, a garment including at least one system for measuring disturbances.

12 Claims, 3 Drawing Sheets

(51) Int. Cl.
  *A61B 5/053* (2021.01)
  *A61N 1/04* (2006.01)
  *D02G 3/44* (2006.01)
  *A61B 5/25* (2021.01)
(52) U.S. Cl.
  CPC ........... *A61N 1/0484* (2013.01); *D02G 3/441* (2013.01); *A61B 2560/0209* (2013.01); *A61B 2560/0214* (2013.01); *D10B 2403/02431* (2013.01)
(58) Field of Classification Search
  CPC .... A61B 2560/0214; A61B 2562/0209; A61N 1/0484; D02G 3/441; D10B 2403/02431
  See application file for complete search history.

(56) References Cited

OTHER PUBLICATIONS

Bibin John et al., "Wireless Blood Pressure Measurement Implant Electronics for Integration in a Stent Graft", Biomedical Engineering, 2016, pp. 155-159.
Tae-Ho Kang, "Textile-Embedded Sensors for Wearable Physiological Monitoring Systems", May 19, 2007, pp. 1-144; URL:https://repository.lib.ncsu.edu/bitstream/handle/1840.16/5143/edt.pdf?sequence=1&isAllowed=y.

* cited by examiner

DISTURBANCES INDICATOR FOR A WEARABLE DEVICE

CROSS REFERENCE TO RELATED APPLICATIONS

This application is a U.S. National Phase Application of International Application No. PCT/FR2017/053832, filed Dec. 22, 2017, which claims the benefit of French Application No. 1663387 filed Dec. 26, 2016, which are both incorporated herein by reference in their entirety.

FIELD OF THE INVENTION

The invention concerns a system for measuring electromagnetic or electrostatic disturbances, intended to be worn by a user. The present invention also concerns a garment comprising such a system.

BACKGROUND

Smart garments enabling measurements of bioelectric signals to be made, require very low-level electrical signals to be passed (on the order of several microvolts to several millivolts) by means of electrical connections of non-negligible length, guided by high contacts impedances. These signals are thus subject to a significant risk of electromagnetic or electrostatic disturbances. These disturbances can be varied. They can be caused by high-frequency radio waves or electrostatic low-frequency disturbances, for example if another person passes close to the sensors. The voltage of the electrical mains is also capable of generating noise at 50 Hz or 60 Hz on the measured and transmitted signals.

These disturbances compromise the use and interpretation of signals, whether performed manually by technicians or physicians, or by informatic means implementing algorithms In the field of medicine, the expertise of the physician may allow different types of artefacts to be distinguished, but only in a limited manner. These electromagnetic or electrostatic disturbances can even distort a diagnosis or make it subject to reservations.

US 2009/318827 describes a system and a method for monitoring the electrical activity of the brain of a subject through a plurality of electrodes placed close to a portion of the body of the subject. Said system further comprises an antenna. The antenna of US 2009/318827 is capable of emitting signals but is not capable of measuring electromagnetic signals.

John et al. describes a system comprising a vascular implant, a pressure sensor and an antenna for wireless transmission of data stored by the sensor to an external analysis unit (Biomedical Engineering, 2016, pp. 155-159). The described antenna is suitable for emitting signals but is not capable of measuring electromagnetic signals.

Kang et al. describes a system for acquisition of physiological signals, comprising a circuit having a plurality of conductive tracks and electronic elements which aim to reduce the output impedance of an electrode connected to said circuit. The conductive tracks are not capable of measuring electromagnetic signals.

EP 2 407 096 describes a textile electrode for measuring body signals, in which a conductive track is used for simplifying the connection between the electrode and the acquisition system. The conductive track described is not capable of measuring electromagnetic signals.

The problem addressed by the present invention is therefore that of providing a system for measuring electromagnetic or electrostatic disturbances, intended to be worn by a user, which can be incorporated in a garment. The present invention thus makes it possible to determine whether the measurements performed on a smart garment are altered by external electromagnetic or electrostatic signals.

SUMMARY

The present invention concerns a method for measuring disturbances, intended to be worn by a user. Said system comprises: at least one bioelectric measurement means; an analogue-to-digital conversion device, electrically connected to said at least one bioelectric measurement means; and at least one conductive track, electrically connected to a ground of the system by means of a resistor, and to an input of the analogue-to-digital conversion device.

In one embodiment of the invention, the length of said conductive track is greater than 1 cm. In an embodiment of the invention, the length of said at least one conductive track is greater than 2 cm, 3 cm, 4 cm, 5 cm, 6 cm, 7 cm, 8 cm, 9 cm, 10 cm or 20 cm, 30 cm, 40 cm or 50 cm.

In one embodiment of the invention, the electrical signal measured by the at least one conductive track is subtracted from an electrical signal measured by the at least one bioelectric measurement means in order to produce a resulting clean signal.

In one embodiment of the invention, a resistor coupled to the conductive track simulates a contact impedance between the skin and at least one bioelectric measurement means.

In one embodiment of the invention, the impedance of said resistor is between 10 kOhms and 100 MOhms. In an embodiment of the invention, the system also comprises a capacitor connected in parallel with said resistor. In an embodiment of the invention, the capacitance of said capacitor ranges between 10 picofarads and 100 nanofarads.

In one embodiment of the invention, the at least one conductive track comprises a first end electrically connected to the ground of the system and to an input of the analogue-to-digital conversion device, and a second, free end.

In one embodiment of the invention, the at least one conductive track comprises a first end electrically connected to the ground of the system and a second end electrically connected to an input of the analogue-to-digital conversion device.

In one embodiment of the invention, said system also comprises a textile or mechanical substrate, wherein said biometric measurement means and said at least one conductive track are mechanically connected to said textile or mechanical substrate.

In one embodiment of the invention, the substrate is a textile substrate and the at least one conductive track:
- comprises at least one conductive thread which is woven, embroidered, knitted or inserted through the textile substrate; or
- is a conductive ink or a conductive paint printed on the textile substrate.

The invention further concerns a garment comprising at least one system for measuring disturbances according to the present invention.

The invention also concerns a method for using the system for measuring disturbances according to the present invention or the garment according to the present invention, comprising the following steps:
- measuring the signal obtained by the at least one bioelectric measurement means;
- measuring the signal obtained by the at least one conductive track; and processing said signals so as to subtract, from the signal measured by the at least one bioelectric measurement means, the signal measured by the at least one conductive track.

DETAILED DESCRIPTION

In the present invention, the terms below are defined in the following manner;
"Garment" refers to any textile capable of being worn by a subject, including a cap.
"Loop antenna" refers to an antenna for measuring the magnetic field of its environment. Its operating principle is the result of an application of the laws of Lenz and Faraday, the voltage induced being proportional to the flux of the magnetic field.
"Device intended to be worn by a user" refers to any garment, item of clothing, cap or undergarment, capable of being worn by user, preferably in contact with the skin.
"Bioelectric measurement means" refers to any sensor capable of measuring an electrical signal produced by a living organism, in contact with or remote from the skin.
"Analogue-to-digital conversion device" refers to an electronic device which transforms an electrical signal into digital data.
"Conductive track" refers to a conductive area. This conductive track may consist of one or more conductive threads, said conductive threads are made of a conductive material or textile threads covered with a conductive surface or a conductive material, preferably textile threads covered with conductive metals such as silver. This conductive track can also be a conductive ink or a conductive paint on a substrate, the conductive ink or paint is filled with electrically conductive material, having flexibility properties enabling this conductive ink or paint to be deposited on flexible surfaces.
"End" refers to the termination of the end portion in the direction of the largest of the dimensions of the conductive track. In the case where the conductive track is a surface, the end is formed by the overhang for connecting to a ground of the system and/or to an input of the analogue-to digital conversion device.
"Substrate" refers to a part providing support to at least one or all of the components of the system according to the invention.
"Textile substrate" refers to a substrate made of insulating textile threads, which can be woven or knitted.
"Mechanical substrate" refers to a substrate made of at least one rigid part, or a part which is not a textile.
"Flexible" refers to the capacity to be bent over a cylindrical part having a radius of 5 to 10 cm without undergoing plastic deformation.

When a range of values is evoked by the expression "between A and B" it is meant that the two cited values, "A" and "B", are included in the range of values evoked. Also included are all values within plus or minus 10% of the limits of the range of values.

Figure 1:
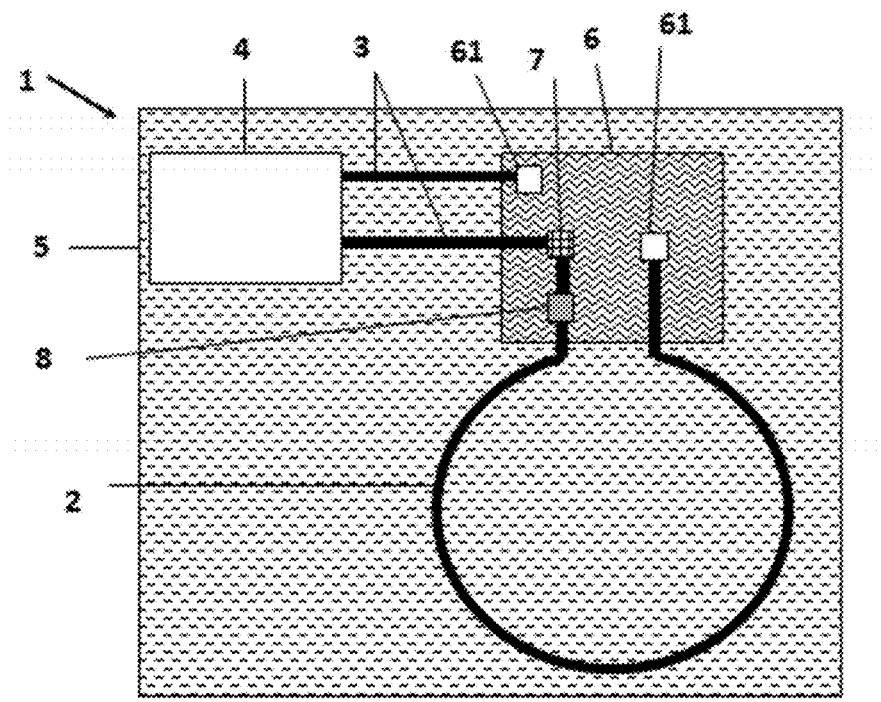
FIG. 1 is a schematic view of the system 1 according to one embodiment of the present invention where the conductive track 2 forms a loop antenna. The conductive track 2 has two ends; a first end is connected to the input 61 of the analogue-to-digital conversion device 6 and a second end is connected to the ground 7 of the system 1.

As illustrated in FIG. 1, the present invention concerns a system for measuring disturbances 1, intended to be worn by a user. This system 1 comprises: at least one bioelectric measurement means 4; an analogue-to-digital conversion device 6 electrically connected to said at least one bioelectric measurement means 4; and at least one conductive track 2 electrically connected to a ground 7 of the system 1 by means of a resistor 8 and to an input 61 of the analogue-to-digital conversion device 6.

The invention concerns a system 1 for measuring disturbances, which is intended to be worn by a user, said system comprising:
at least one bioelectric measurement means 4 for measuring a body electrical signal and capable of receiving external electromagnetic and/or electrostatic disturbances;
an analogue-to-digital conversion device 6 electrically connected to said at least one bioelectric measurement means 4; and
at least one conductive track 2 for measuring electromagnetic and/or electrostatic signals, said conductive track 2 being electrically connected to a ground 7 of the system 1 by means of a resistor 8 and to an input 61 of the analogue-to-digital conversion device 6.

The at least one bioelectric measurement means 4 can measure electrical signals emitted by the human or animal body. In an embodiment, this means is a metal or conductive electrode in contact with the skin and capable of measuring very weak variations of electrical signals, such as those measured by electroencephalography (EEG), electrocardiography (ECG) or electromyography (EMG). In an embodiment, the measurement means can also be an electrooculogram (EOG) sensor or a means for detecting light stimuli.

According to the present invention, the at least one bioelectric measurement means 4 is electrically connected to the analogue-to-digital conversion device 6 by an electrical connection 3. Said analogue-to-digital conversion device 6 is configured to convert the electrical signal coming from the at least one bioelectric measurement device 4 into digital values.

The conductive track 2 according to the present invention plays the role of an antenna. It must therefore extend over a sufficient length or area in order to detect the electromagnetic and/or electrostatic disturbances which are also recorded by the at least one bioelectric measurement means 4 and which disturb the measured signal. The length or area of this conductive track 2 must therefore be sufficiently long and its purpose goes beyond a simple electrical connection between two components.

The conductive track 2 is electrically connected to the ground 7 of the system 1 and to an input 61 of the analogue-to-digital conversion device 6. In this way, the analogue-to-digital conversion device 6 is able to convert the electrical signal coming from the conductive track 2 into digital values.

In one embodiment, the conductive track 2 is a conductive path in which two dimensions have a negligible distance with respect to the distance of the third dimension.

In one embodiment illustrated in FIG. 1, said conductive track 2 is electrically connected to the ground 7 of the system 1 by a first end and is electrically connected to an input 61 of the analogue-to-digital conversion device 6 by a second end. In one embodiment, the conductive track 2 comprises a first end electrically connected to the ground 7 of the system 1 and a second end electrically connected to an input 61 of the analogue-to-digital conversion device 6.

Figure 2:
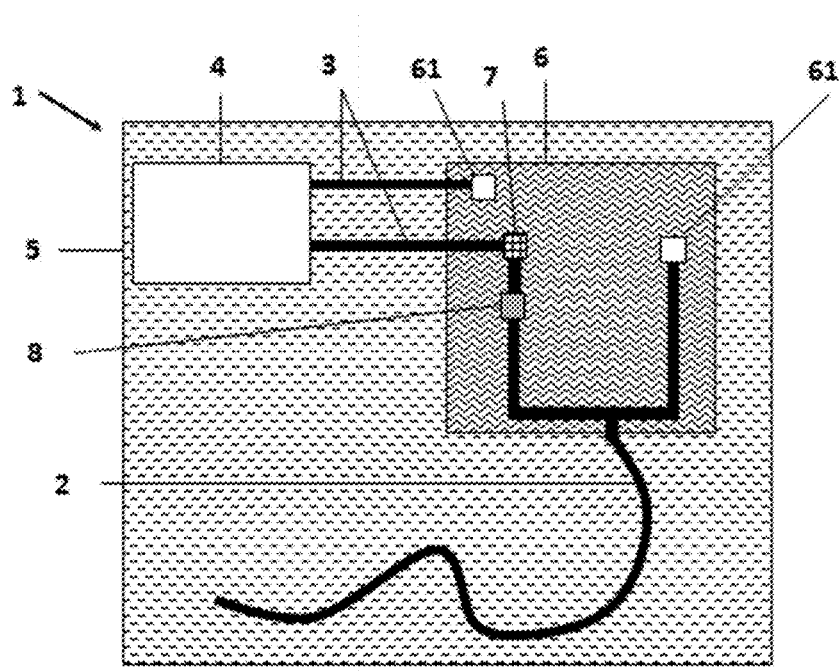
FIG. 2 is a schematic view of the system 1 according to one embodiment of the present invention where the conductive track 2 does not form a closed circuit. The conductive track 2 has a first end connected to the input 61 of the analogue-to-digital conversion device 6 and connected to the ground 7 of the system 1. The conductive track 2 comprises a second end which is not connected to a resistor or any electrically conductive element, so as to create an open circuit.

In one alternative embodiment illustrated in FIG. 2, said conductive track 2 comprises at least two ends, the first end is electrically connected to the ground 7 of the system 1 and to an input 61 of the analogue-to-digital conversion device 6, and the second end is free. In this embodiment, the conductive track comprises a first end electrically connected to the ground 7 of the system 1 and to an input 61 of the analogue-to-digital conversion device 6, and a second, free end. "The second end is free" shall mean that this end is not connected to any resistor or other electrically conductive element, so as to create an open circuit. In an embodiment, the first end is connected to an input of a printed circuit and said printed circuit input is electrically connected to the ground of the system 7 and to an input 61 of the analogue-to-digital conversion device 6.

In one embodiment that is not illustrated, the conductive track 2 comprises a plurality of free ends.

The conductive track 2 must have a sufficiently large length in order to enable the measurement of disturbances. In an embodiment, the conductive track 2 has a length greater than 1 cm, 2 cm, 3 cm, 4 cm, 5 cm, 6 cm, 7 cm, 8 cm, 9 cm, 10 cm 20 cm, 30 cm, 40 cm or 50 cm. In one embodiment, the conductive track 2 has a length comprised between 5 cm and 500 cm, or between 5 cm and 200 cm. In an embodiment, the conductive track 2 has a length comprised between 5 cm and 100 cm. In an embodiment, the maximum length of the conductive track 2 is not limited.

This length enables a greater precision in the measurement of the disturbances, for example electromagnetic or electrostatic disturbances which come from the body of the user wearing the system 1 according to the invention.

Indeed, the conductive track 2 must have a sufficient length to record the disturbances.

In an alternative embodiment that is not illustrated, the role of antenna is performed by an area surrounded by a conductive track 2 electrically connected to the analogue-to-digital conversion device 6 and to a ground of the system 7. The conductive track 2 must therefore surround a sufficiently large area in order to enable the measurement of the disturbances. In this embodiment, the area surrounded by the conductive track 2 has an area greater than 1 cm$^2$. In one embodiment, the area surrounded by the conductive track 2 has an area greater than 10, 20, 30, 40, 50, 100, 200 or 300 cm$^2$.

In one embodiment, the conductive track 2 extends on a textile or mechanical substrate 5.

In one embodiment where the substrate 5 is a textile substrate 5, the conductive track 2 is produced so as to have the same flexibility as the textile substrate 5. The conductive track 2 must be able to be folded on itself without undergoing plastic deformation and without undergoing deteriorations which could lead to a break in the electrical connection. In one embodiment, the conductive track 2 has a flexibility allowing it to be bent over a cylindrical part having a radius of 5 to 10 cm without undergoing plastic deformation.

In an embodiment, the conductive track 2 forms a loop antenna. In this same embodiment, the shape drawn by the conductive track 2 can be an oval, circular, rectangular, triangular or ellipsoidal shape, or any other shape.

In one embodiment, the bioelectric measurement means 4 can be situated inside the shape drawn by the conductive track 2. In one embodiment, the bioelectric measurement means 4 can be situated substantially at the centre of the shape drawn by the conductive track 2. The position of the bioelectric measurement means 4 inside the shape drawn by the conductive track 2 enables a better indication of the electromagnetic and/or electrostatic disturbances measured by the at least one bioelectric measurement means 4, since these disturbances will be measured closer to the at least one bioelectric measurement means 4.

In one embodiment, the electrical signal measured by the at least one conductive track 2 is subtracted from an electrical signal measured by the at least one bioelectric measurement means 4 in order to produce a resulting clean signal.

According to the present invention, the analogue-to-digital conversion device 6 is configured to convert the electrical signal coming from the conductive track 2 and the electrical signal coming from the at least one bioelectric measurement device 4 into digital values.

The digital values coming from the conductive track 2 correspond to the electromagnetic and/or electrostatic disturbances also recorded by the at least one bioelectric measurement means 4. By subtracting the values coming from the conductive track 2 from the values coming from the at least one bioelectric measurement means 4, are obtained the values of a signal from which parasitic external signals have been removed.

In a particular embodiment, the system 1 also comprises a means (such as an electronic device or an algorithm) which makes it possible to subtract the values coming from the conductive track from the values coming from the at least one bioelectric measurement means 4. In another embodiment, this operation can be performed a posteriori or, more simply, the person responsible for interpreting the measurements can compare the two values in order to facilitate his/her interpretation of the values coming from the at least one bioelectric measurement means 4.

In an embodiment that is not illustrated, the system 1 also comprises a printed circuit and the analogue-to-digital conversion device 6 is integrated on this printed circuit.

According to the present invention, the at least one conductive track 2 is linked or electrically connected to the ground of the system 7 via a resistor 8. This resistor 8 makes it possible to perform the measurement of the electrical signal coming from the conductive track 2. Indeed, the low frequencies cannot be measured without resistance.

In one embodiment, the impedance of the resistor 8 must be of the same order of magnitude as, and preferably as close as possible to, the contact impedance between the skin and the at least one bioelectric measurement means 4. Thus, the electrical signals measured by the conductive track 2 can be compared with the signals measured by the at least one bioelectric measurement means 4.

In one embodiment, the conductive track 2 is configured to receive signals such as electromagnetic and/or electrostatic signals.

In an embodiment, the conductive track 2 is configured to emit signals such as electromagnetic and/or electrostatic signals.

In one embodiment, the resistor coupled to the conductive track 2 simulates a contact impedance between the skin and at least one bioelectric measurement means 4.

In one embodiment where the at least one bioelectric measurement means 4 is a dry EEG electrode, the order of magnitude of the contact impedance between the skin of the user and the dry EEG electrode is between 100 kOhm and 10 MOhm (10 Megaohms).

In one embodiment, the impedance of said resistor 8 ranges between 10 kOhm and 100 MOhm. In a preferred embodiment, the impedance of said resistor 8 is between 100 kOhm and 10 MOhm, preferably between 500 kOhm and 5 MOhm, very preferably between 700 kOhm and 2 MOhm, yet more preferably between 800 kOhm and 1.5 MOhm.

In one embodiment illustrated in FIG. 1 and FIG. 2, the resistor 8 is part of the analogue-to-digital conversion device 6. In another embodiment illustrated in FIG. 5, the resistor 8 is not integrated in the analogue-to-digital conversion device 6 but is attached on the substrate 5, in contact with the conductive track 2. In one embodiment that is not illustrated, the resistor is not attached to the analogue-to-digital conversion device 6 but is integrated in a printed circuit comprising the analogue-to-digital conversion device 6.

Figure 3:
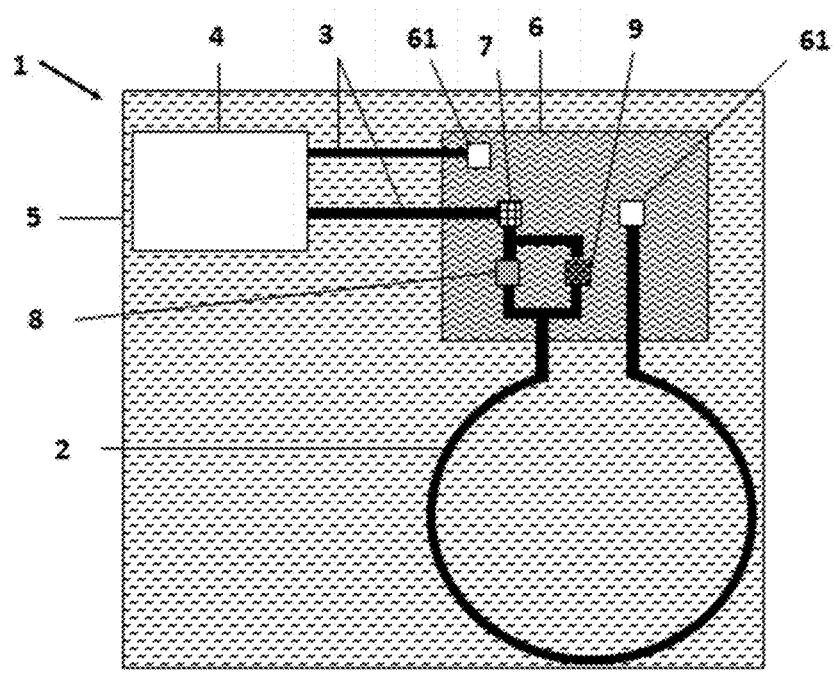
FIG. 3 is a schematic view of the system 1 according to one embodiment of the present invention according to FIG. 1, wherein a capacitor 9 is mounted in parallel with the resistor 8.
Figure 4:
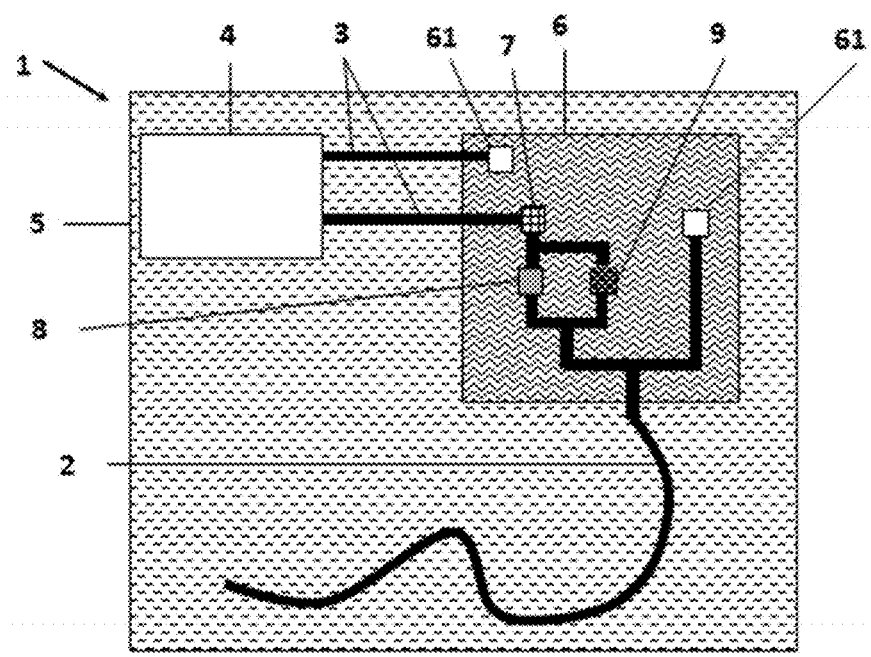
FIG. 4 is a schematic view of the system 1 according to one embodiment of the present invention according to FIG. 2, wherein a capacitor 9 is mounted in parallel with the resistor 8.

In one embodiment illustrated in FIG. 3 and FIG. 4, in order to get closer to the contact impedance between the skin and the at least one bioelectric measurement means, the system 1 comprises a capacitor 9 mounted in parallel with the resistor 8. This capacitor 9 makes it possible to model the parasitic capacitance between the skin and the at least one bioelectric measurement means 4. The capacitance of the capacitor 9 must be of the same order of magnitude as, and preferably as close as possible to, the parasite capacitance of the contact between the skin and the at least one bioelectric measurement means 4. Thus, the electrical signals measured by the conductive track 2 can be compared with the signals measured by the at least one bioelectric measurement means 4. The order of magnitude of the capacitance of said capacitor 9 is variable depending on the bioelectric measurement means 4 used. In one embodiment, said capacitor 9 has a capacitance between 10 picofarads and 100 nanofarads.

Figure 5:
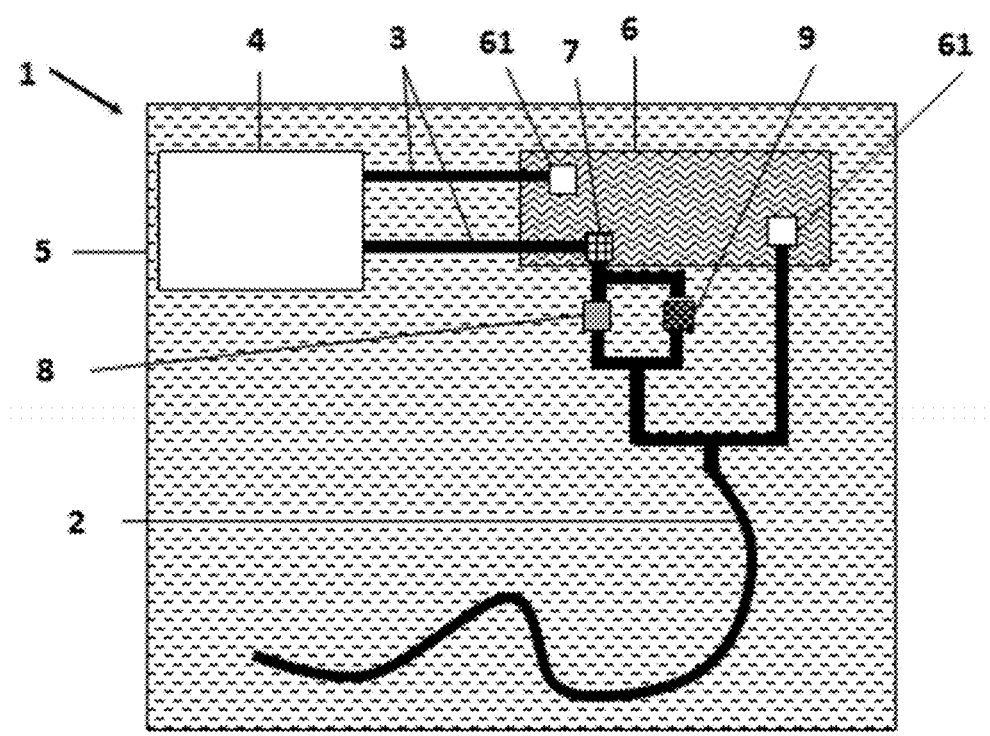
FIG. 5 is a schematic view of the system 1 according to one embodiment of the present invention according to FIG. 4, wherein the resistor 8 and the capacitor 9 are mounted on the textile or mechanical substrate 5 and not on the analogue-to-digital conversion device 6. The figures have been produced for pedagogic purposes, in order to allow a reader of the present patent application to better identify the invention. The figures are therefore not to scale and the scope of said patent application cannot be considered to be limited by the distances measured on the figures.

In another embodiment illustrated in FIG. 5, the resistor 8 and the capacitor 9 are not integrated in the analogue-to-digital conversion device 6 but are attached on the substrate 5, in contact with the conductive track 2. In one embodiment that is not illustrated, the resistor 8 and the capacitor 9 are not integrated in the analogue-to-digital conversion device 6 but are integrated on a printed circuit comprising the analogue-to-digital conversion device 6.

In one embodiment, the system 1 comprises a textile or mechanical substrate 5 on which the bioelectric measurement means 4, the analogue-to-digital conversion device 6 and the conductive track 2 are mounted. In one embodiment, the system 1 comprises a textile or mechanical substrate 5, and said biometric measurement means 4 and said conductive track 2 are mechanically connected to said textile or mechanical substrate 5. This substrate 5 makes it possible to ensure the cohesion of the various components of the system 1. In one embodiment, the analogue-to-digital converter is also mechanically connected to the substrate 5.

In one embodiment, the substrate 5 is a mechanical substrate 5. The mechanical substrate 5 may be a plate made of plastic material or, more generally, be any support comprising an insulating contact surface with the conductive track 2. In one embodiment, the mechanical substrate 5 is a mechanical framework which can be used in order to produce a headset. The mechanical substrate 5 can be rigid or flexible.

In another embodiment, the substrate 5 is a textile 5 substrate. In one embodiment, the textile substrate 5 is a woven or knitted substrate with insulating threads.

In one embodiment, the substrate 5 is a textile substrate 5. The use of the textile substrate 5 makes it possible to provide the system 1 with its properties of flexibility and elasticity. In this same embodiment, the conductive track 2 is produced so as to have substantially the same flexibility as the textile substrate 5. In one embodiment where the substrate 5 is a textile substrate 5, and the conductive track 2 comprises at least one conductive thread that is woven, embroidered, knitted or inserted through the textile substrate 5. In this same embodiment, the at least one conductive thread is made of a conductive material or at least one textile thread covered with a conductive surface, preferably covered with a conductive metal such as silver. In an alternative embodiment, the conductive track 2 is a conductive ink or a conductive paint printed on the textile substrate 5.

In one embodiment, the conductive track 2 is delimited by its ends. In one embodiment, the conductive track 2 is delimited by its junction with the analogue-to-digital conversion device 6. In another embodiment, the conductive track 2 is delimited by its junction with the resistor, the input 61 of the analogue-to-digital conversion device 6 and, optionally, the capacitor 9. In one embodiment, the conductive track 2 is delimited by the point of connection with the printed circuit.

In one embodiment, the system 1 comprises a plurality of conductive tracks 2.

The ground 7 is the reference branch of the electrical potentials. The ground 7 can be located on the analogue-to-digital conversion device 6 or elsewhere on the system 1 according to the present invention, for example on the substrate 5.

The invention further relates to a garment comprising at least one system 1 for measuring disturbances according to the present invention. "Garment" shall mean any textile capable of being worn by a subject, including a cap. In a preferred embodiment, said garment is intended to be worn in contact with the skin, so as to facilitate the reliability of the measurement recorded by the at least one bioelectric measurement means 4, such as an undergarment, a cap, a shirt or a T-shirt.

In one embodiment, the invention is applied to an already existing measurement device, such as an EEG or other headset.

In one embodiment, the garment is a cap which comprises two systems 1 according to the present invention. In this embodiment, the two systems 1 according to the present invention are arranged on either side of the cap. The user can therefore arrange one system 1 in contact with the left side of his cranium and one system 1 in contact with the right side of his cranium.

According to one embodiment, the garment according to the present invention can measure external electromagnetic and/or electrostatic disturbances to which the at least one bioelectric measurement means 4 is exposed.

The invention also concerns a method for using the system for measuring disturbances 1 according to the present invention, comprising the following steps:

measuring the signal obtained by the at least one bioelectric measurement means 4;
 measuring the signal obtained by the at least one conductive track 2; and
 processing said signals so as to subtract, from the signal measured by the at least one bioelectric measurement means, the signal measured by the at least one conductive track 2.

The step of processing said signals can be carried out by an algorithm, an electronic module, a data processing system or by a technician

The invention claimed is:

1. A system for measuring disturbances, which is intended to be worn by a user, said system comprising:
 at least one bioelectric measurement means configured to measure a body electrical signal and to receive external electromagnetic and/or electrostatic disturbances;
 an analogue-to-digital conversion device electrically connected to said at least one bioelectric measurement means; and
 at least one conductive track for measuring electromagnetic and/or electrostatic signals, said conductive track being electrically connected to a ground of the system by means of a resistor, and to an input of the analogue-to-digital conversion device,
 a substrate chosen among a textile substrate and/or mechanical substrate configured to be worn on the body of the user, wherein the biometric measurement means and the conductive track are mechanically connected to said substrate.

2. The system according to claim 1, wherein the electrical signal measured by the at least one conductive track is subtracted from an electrical signal measured by the bioelectric measurement means in order to produce a resulting signal from which parasitic external signals have been removed.

3. The system according to claim 1, wherein a resistor coupled to the conductive track simulates a contact impedance between the skin and the bioelectric measurement means.

4. The system according to claim 1, wherein the length of said conductive track is greater than 1 cm.

5. The system according to claim 1, wherein the impedance of the resistor ranges between 10 kOhm and 100 MOhm.

6. The system according to claim 1, further comprising a capacitor connected in parallel with the resistor.

7. The system according to claim 6, wherein the capacitance of the capacitor ranges between 10 picofarads and 100 nanofarads.

8. The system according to claim 1, wherein the conductive track comprises a first end electrically connected to the ground of the system and to an input of the analogue-to-digital conversion device, and a second, free end.

9. The system according to claim 1, wherein the conductive track comprises a first end electrically connected to the ground of the system and a second end electrically connected to an input of the analogue-to-digital conversion device.

10. The system according to claim 1, wherein the substrate is a textile substrate and the conductive track:
 comprises at least one conductive thread which is woven, embroidered, knitted or inserted through the textile substrate; or
 is a conductive ink or a conductive paint printed on the textile substrate.

11. A garment comprising at least one system for measuring disturbances according to claim 1.

12. A method for using the system for measuring disturbances according to claim 1 or a garment comprising at least one of said system for measuring disturbances comprising the following steps:
 measuring the signal obtained by the at least one bioelectric measurement means;
 measuring the signal obtained by the at least one conductive track; and
 processing said signals so as to subtract, from the signal measured by the bioelectric measurement means, the signal measured by the conductive track.

* * * * *